(12) United States Patent
Stavig et al.

(10) Patent No.: US 6,372,189 B1
(45) Date of Patent: Apr. 16, 2002

(54) EJECTOR DISCHARGE SAFETY CHUTE

(75) Inventors: Tracy Stavig, Madera; Joost Veltman, Aptos, both of CA (US)

(73) Assignee: EMC Corporation, Chicago, IL (US)

( * ) Notice: Subject to any disclaimer, the term of this patent is extended or adjusted under 35 U.S.C. 154(b) by 0 days.

(21) Appl. No.: 09/303,773

(22) Filed: Apr. 30, 1999

(51) Int. Cl.⁷ .............................................. A61L 2/24
(52) U.S. Cl. ................... 422/302; 426/521; 99/360; 99/361; 99/362; 99/365; 422/297; 422/27
(58) Field of Search ........................... 221/13, 21, 80, 221/81, 82; 99/360, 361, 362, 483; 141/21; 222/21, 22, 41, 47, 49; 53/58, 500; 422/26, 28, 302–304; 134/134

(56) References Cited

U.S. PATENT DOCUMENTS 4,677,283 A * 6/1987 Lewis .......................... 235/98
5,705,218 A * 1/1998 Veltman .................... 426/521

OTHER PUBLICATIONS

"Rotary Atmospheric Cookers/Coolers," FMC Corporation brochure (1992).
Canning Trade Handbook, pp. 74–75, 86–88.

* cited by examiner

Primary Examiner—Robert J. Warden, Sr.
Assistant Examiner—Sean E. Conley
(74) Attorney, Agent, or Firm—Flehr Hohbach Test Albritton Herbert

(57) ABSTRACT

A safety sensor mechanism (10) for a rotary sterilizer (16) including a slider plate (40) positioned in the revolving path of cans (11) and movable away from a discharge opening (28) of the sterilizer. The safety mechanism includes slider bars (44) and tubular housings (48) with coil springs (50) for creating a spring-loaded slider plate that yields if engaged by a misaligned can that does not proper eject from the sterilizer.

22 Claims, 4 Drawing Sheets

EJECTOR DISCHARGE SAFETY CHUTE

TECHNICAL FIELD

The present invention pertains to ejector discharge mechanisms within rotary sterilizers and coolers used to process canned products, such as canned fruits and vegetables. More particularly, the present invention pertains to a safety device that provides an automatic shutdown signal to the rotary sterilizer or cooler when cans are not properly discharging from the sterilizer or cooler.

BACKGROUND OF THE INVENTION

A common device and method for discharging cans from an atmospheric rotary sterilizer is a star wheel that includes pairs of spaced-apart teeth that, when rotated, engage both chimes of a can to eject the can from the sterilizer. Ejected cans roll onto a discharge chute where sensors are positioned to monitor the cans as they roll out of the sterilizer. If the cans back up on the discharge chute, the sensors provide a signal to alert an operator or provide for automatic equipment shutdown.

However, it is not uncommon for cans to become damaged or deformed during processing and, as a result, not properly move within the spiral rail of a rotary sterilizer. For example, a damaged can may become lodged, as it revolves around the rotary sterilizer shell, between the upper edge of the spiral rail and the interior wall of the shell. When the teeth of the star wheel move around to engage the can and push it out of the sterilizer, the teeth miss the chimes, and may do further damage to the can. Either way, the can is not pushed out of the sterilizer and continues to revolve with the reel until it gets squashed at the end of the shell, which causes a major shutdown situation. An operator needs to stop the sterilizer, reverse the reel and reach into the shell to manually remove the damaged can.

SUMMARY OF THE INVENTION

Briefly described, the rotary sterilizer of the present invention includes a safety apparatus for monitoring proper discharge of cans from a rotary sterilizer having a rotary reel, a plurality of reel angles at the periphery of the rotary reel for moving the cans around a revolving path within the sterilizer, a spiral rail for guiding the cans from one end of the sterilizer to the other end along a spiral path, a discharge chute for receiving discharged cans from the sterilizer, and an ejector for discharging the cans onto the discharge chute. The safety apparatus includes a sensor positioned to detect the presence of a can that does not properly discharge from the sterilizer.

According to an aspect of the invention, the safety apparatus comprises a discharge chute extension that projects into the revolving path of the cans and is movable in reaction to engagement with a can that is not discharged by the ejector. Movement of the discharge chute extension provides an indication that a can has not properly discharged from the sterilizer and therefor needs to be manually retrieved from within the sterilizer.

According to an aspect of the invention, the discharge chute extension is positioned in the revolving path of the cans at a point for engagement with cans not properly discharged onto the discharge chute. Preferably, the discharge chute extension is movable at least partially in the direction of movement of a revolving can.

According to another aspect of the invention, the discharge chute extension forms part of the discharge chute. In this embodiment, the discharge chute extension is movable out of the revolving path of the cans upon engagement with a can not properly discharged.

According to another aspect of the invention, the discharge chute extension is movable along a linear path that is provided by a guide mechanism that limits movement of the discharge chute extension along the linear path. Preferably, the discharge chute extension includes a limit device for limiting the length of movement of the discharge chute extension.

According to another aspect of the invention, the discharge chute extension includes a sensor for detecting movement of the discharge chute extension.

According to another aspect of the invention, the discharge chute extension includes a spring bias against which a non-discharged can must work to move the extension. Preferably, the spring bias is adjustable to accommodate different size cans.

These and other features, objects, and advantages of the present invention will become apparent from the following description of the best mode for carrying out the invention, when read in conjunction with the accompanying drawings, and the claims, which are all incorporated herein as part of the disclosure of the invention.

BRIEF DESCRIPTION OF THE DRAWINGS

In the drawings, like reference numerals refer to like parts throughout the several views, wherein.

DETAILED DESCRIPTION OF THE INVENTION

Figure 1:
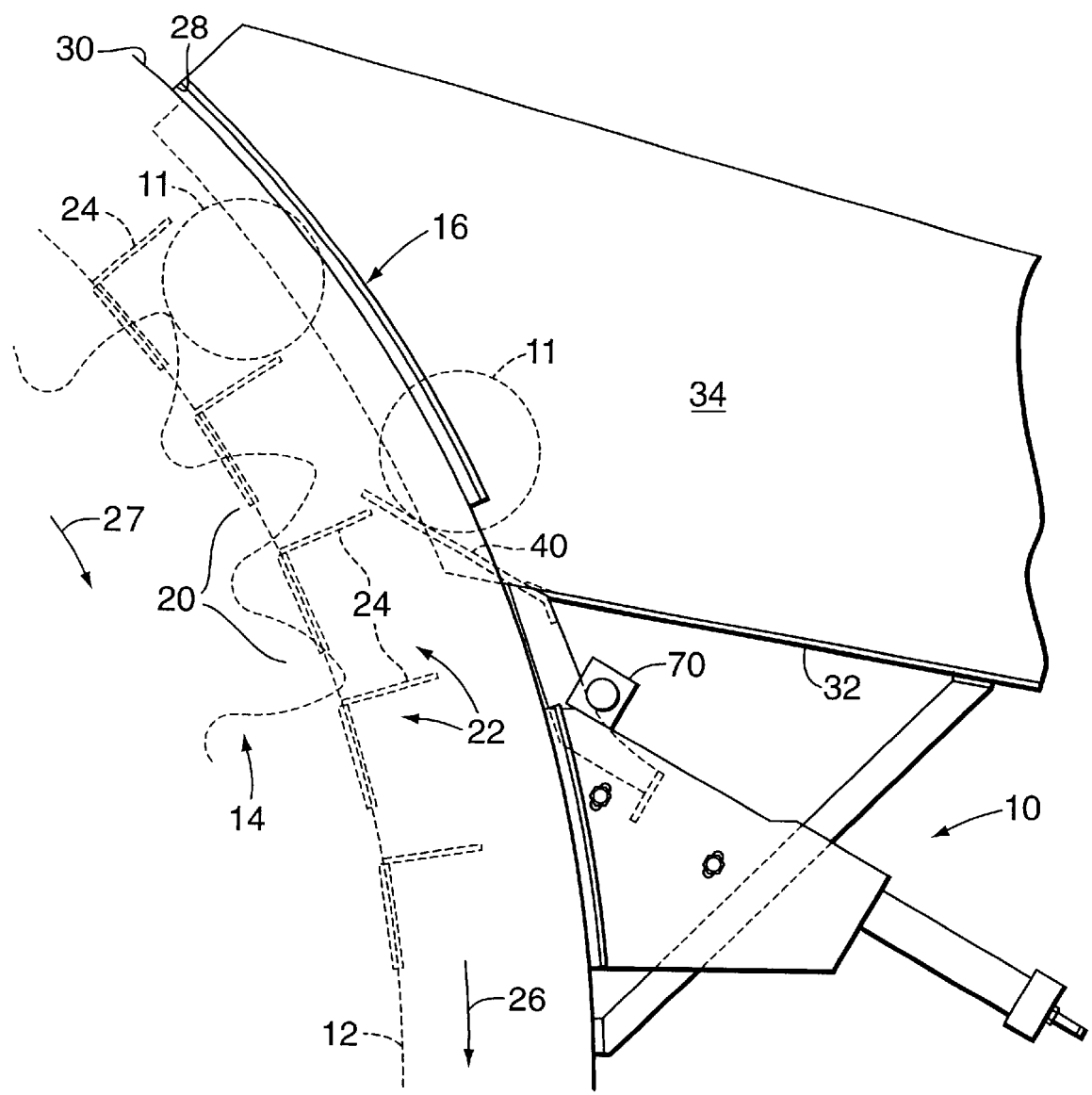
FIG. 1 is sectional elevation view of a portion of a rotary sterilizer and its ejector star wheel.

Reference will now be made in detail to the preferred embodiments of the invention, examples of which are illustrated in the accompanying drawings. While the invention will be described in conjunction with the preferred embodiments, it will be understood that the described embodiments are not intended to limit the invention specifically to those embodiments. On the contrary, the invention is intended to cover alternatives, modifications and equivalents, which may be included within the spirit and scope of the invention as defined by the appended claims.

A principal feature of this device is a spring loaded discharge chute safety mechanism, generally indicated at 10, that yields in the event of a can 11 being misaligned and failing to be lifted from a reel 12 by an ejector star wheel 14 of a rotary sterilizer 16. The design of rotary sterilizer 16 forms no part of the inventive aspect of the present invention and is of the type generally known in the food processing industry. The assignee of the present invention, Food Machinery Corporation of Chicago, Ill. USA manufactures and sells such atmospheric sterilizers. Generally, the present invention is compatible with any rotary processing equipment that has an internal ejector for discharging cans from the device out onto a discharge chute. Such equipment includes sterilizers, cookers, coolers, and pre-heaters. The term "sterilizer" when used herein is meant to include any of these types of machines, unless otherwise noted.

Star wheel ejector 14 works by interaction of its lobes 20 with pockets 22 formed by angle irons 24 of reel 12. Sterilizer 16 includes a parallel cooker heads and a mounted adjustable segment face (not shown) that supports the shaft of star wheel ejector 14. The star wheel ejector shaft is mounted in bearings that are spaced around the adjustable segment face of the sterilizer head to support this shaft. The ejector stars are then mounted on this shaft and aligned with the reel cut out features which are located in line with the last turn of the cooker spiral. The ejector star is directly driven by the angle irons of the reel.

As reel 12 rotates in the direction of arrow 26 and star wheel ejector 14 rotates in the direction of arrow 27, lobes 20 move into slots (not shown) of reel 12 and into pockets 22 formed by the angle irons, thereby engaging cans 11 and pushing the cans outwardly through an opening 28 in the shell 30 of sterilizer 16. As cans 11 are pushed out of the sterilizer, they land onto a discharge chute 32, which extends away from the sterilizer and leads to a subsequent, downstream processing station. Discharge chute 30 angles downward slightly to promote rolling of the cans away from the sterilizer and includes sidewalls 34 to contain the cans on the discharge chute.

Since on occasion faulty cans get fed into this machine, these cans have a large probability of being misaligned with the lobes of the star wheel ejector. In the rare event of misaligned cans, the lobes 20 of star wheel ejector 14 can be longitudinally or angularly misaligned with the chimes of the cans. As a result, the cans are not pushed outwardly by the lobes and get caught between an angle iron 24 and the forward end of discharge chute 32. This event has the potential of damaging the angle irons, as well as the star wheel ejectors. The discharge chute safety mechanism 10 is provided to prevent such an occurrence.

Figure 2:
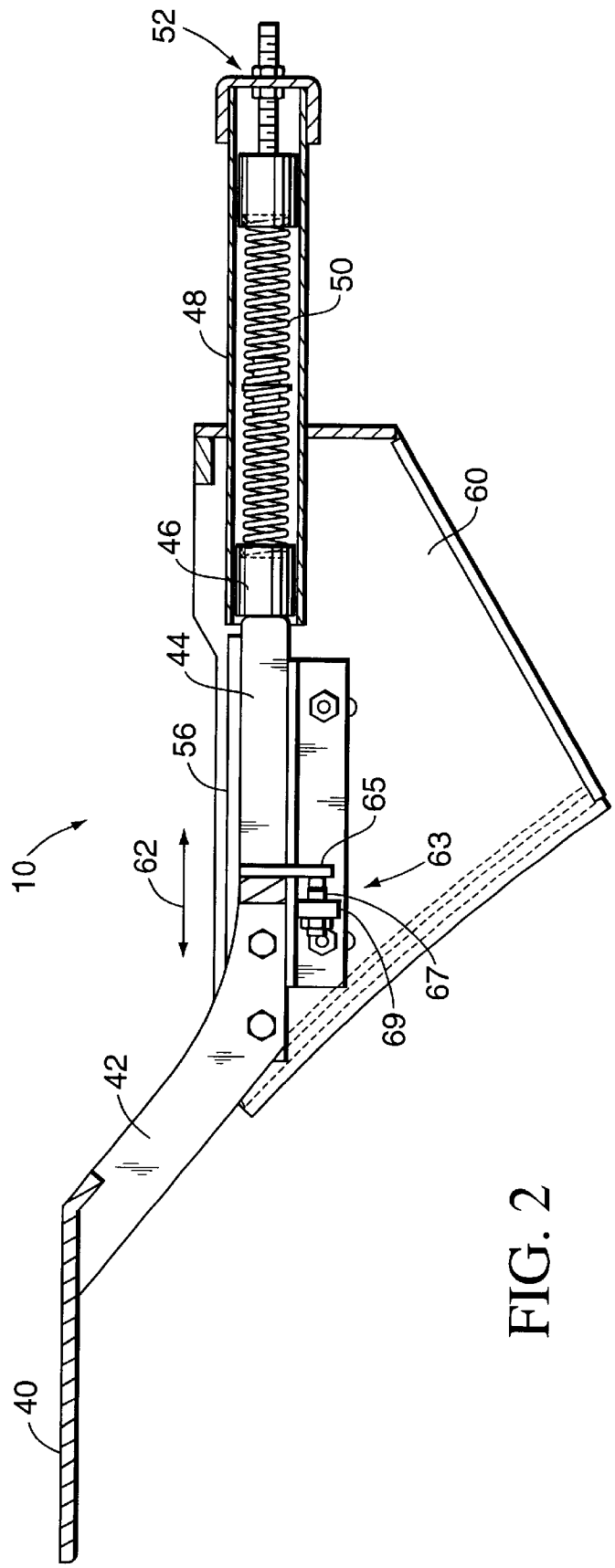
FIG. 2 is an enlarged sectional elevation view of the ejector discharge safety chute.

Referring to FIG. 2, discharge chute safety mechanism 10 includes a rectangular slider plate 40 that forms the forward surface of the discharge chute. Slider plate 40 extends into the discharge opening of the sterilizer to receive discharged cans. A rectangular frame component 42 supports slider plate 40 and is in turn carried by a pair of laterally spaced slider bars 44 (only one shown). Each slider bar 44 is mounted to a slider block 46 that is linearly movable within a tubular housing 48.

A coil spring 50 in each housing biases slider blocks 46 to the left as shown, which biases slider bars 44 to the left and, in turn, biases slider plate 40 into an extended position that positions the forward edge 68 of the slider plate into the opening of the sterilizer. A coil spring adjuster in the form of a threaded bolt and nut assembly 52 provides for adjustment of the bias of coil springs 50.

Slider bars 44 fit into side slots of mounting rails 56, which in turn are mounted to a U-shaped slider bracket 60 that is mounted to the shell of the sterilizer and supports the discharge chute safety mechanism. The slots of mounting rails 56 and tubular housings 48 restrict movement of slider bars 44 and slider plate 40 to linear movement in the direction of arrow 62.

A slider bar limiter assembly 63 is provided for limiting extension of slider plate 40 into the discharge opening of the sterilizer. Assembly 63 includes a pair of downwardly extending limit bars 65 (only one shown) that are secured to frame assembly 42 and a pair of adjustable bolts 67 that are threadably secured to brackets 69, which in turn are mounted to slider bracket 60. Adjustment of bolts 67 forward and backward adjusts the forward extension of slider plate 40 into the discharge opening. Thus, the discharge chute trigger force can be set up to meet the requirements for different can configurations.

Figure 3:
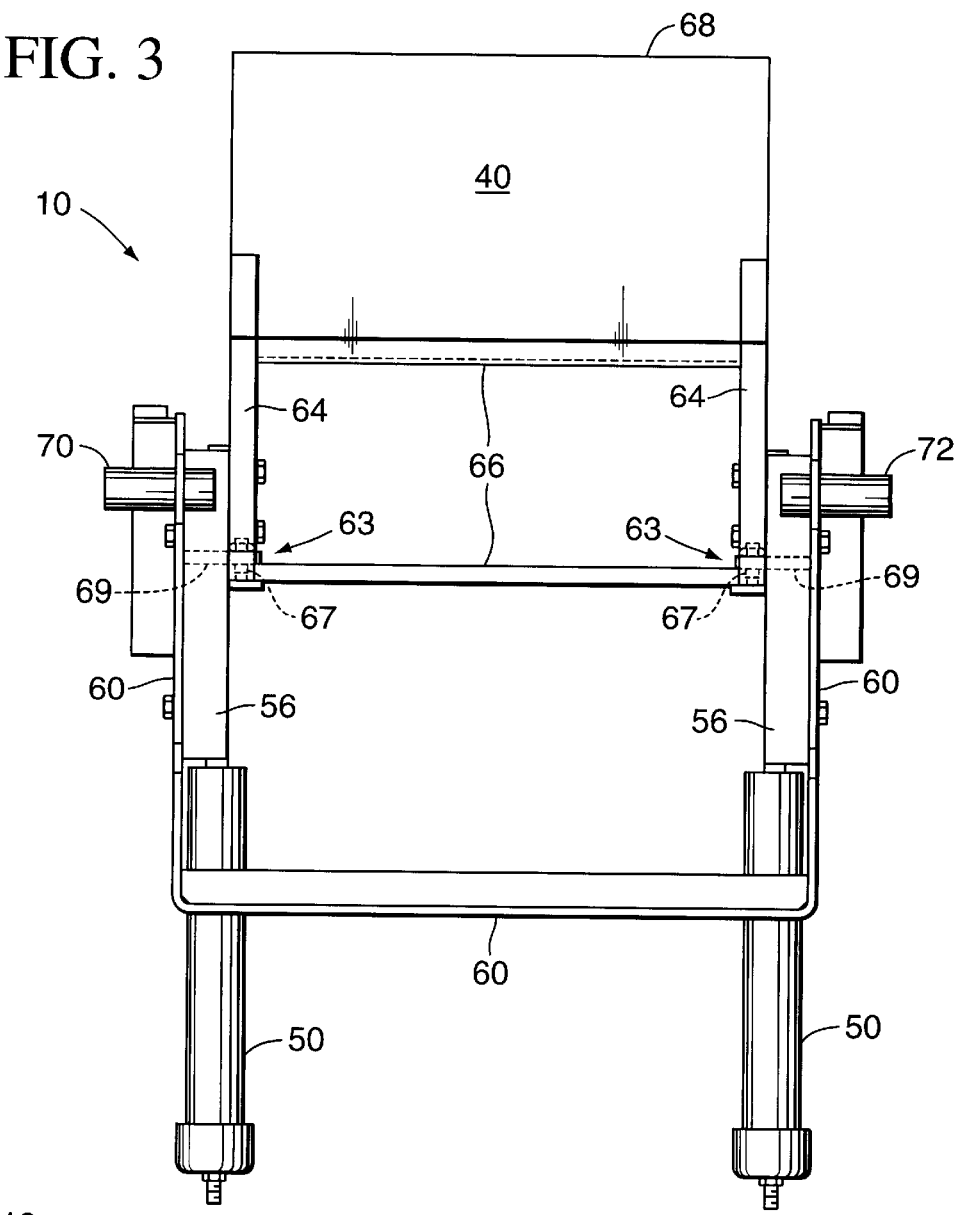
FIG. 3 is plan view of the ejector discharge safety chute.
Figure 4:
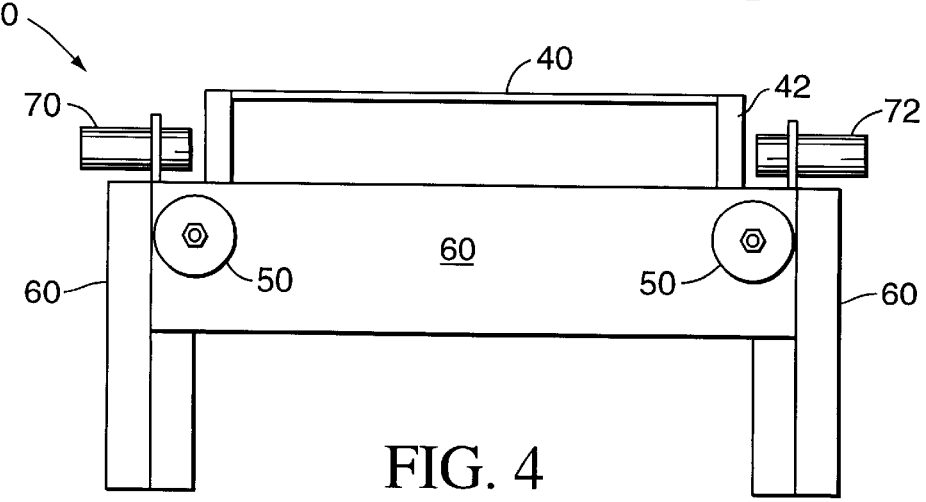
FIG. 4 is an end elevation view of the ejector discharge safety chute.

FIGS. 3 and 4 provide additional illustration of the arrangement of discharge chute safety mechanism 10. Rectangular frame component 42 includes two parallel side supports 64 held in place by parallel transverse braces 66. Side supports 64 are secured to mounting rails 56, which in turn are mounted to U-shaped slider bracket 60. U-shaped slider bracket 60 carries tubular housings 50 in spaced-apart, parallel orientation, which provides equal spring bias to both sides of slider plate 40. This ensures that the leading edge 68 of slider plate 40 is properly aligned within the sterilizer so that it can both (1) receive properly discharged cans and, (2) engage a misaligned can, as discussed in more detail later.

The width of slider plate 40 approximates the width of the discharge opening of the sterilizer. Some sterilizers are set up with dual spiral paths so that two lines of cans are processed simultaneously. For this arrangement, the star wheel ejector includes two ejector mechanisms, one for each line of cans. Also, the discharge opening is wide enough for two cans to be discharged together. Accordingly, for dual-line sterilizers, the slider plate 40 needs to be wide enough to span both lines of cans so that if either can is misaligned, the slider plate will contact that can.

Discharge chute safety mechanism 10 also includes a pair of sensors 70, 72 (FIG. 4) that are secured at the forward end and on either side of slider bracket 60. Sensors 70, 72 detect rearward linear movement of frame assembly 42 caused by contact of slider plate 40 with a misaligned can, which in turn signals the control system to trigger the sterilizer braking device and stops the line. This allows removal of the faulty cans that caused the problem.

With the foregoing arrangement, the slider plate forms a spring-loaded chute entry mechanism that will yield, protecting the critical ejector star and angle irons. It does this by allowing a portion of the discharge chute to move away from the reel if a damaged can fails to clear the reel when being discharged.

Figure 5:
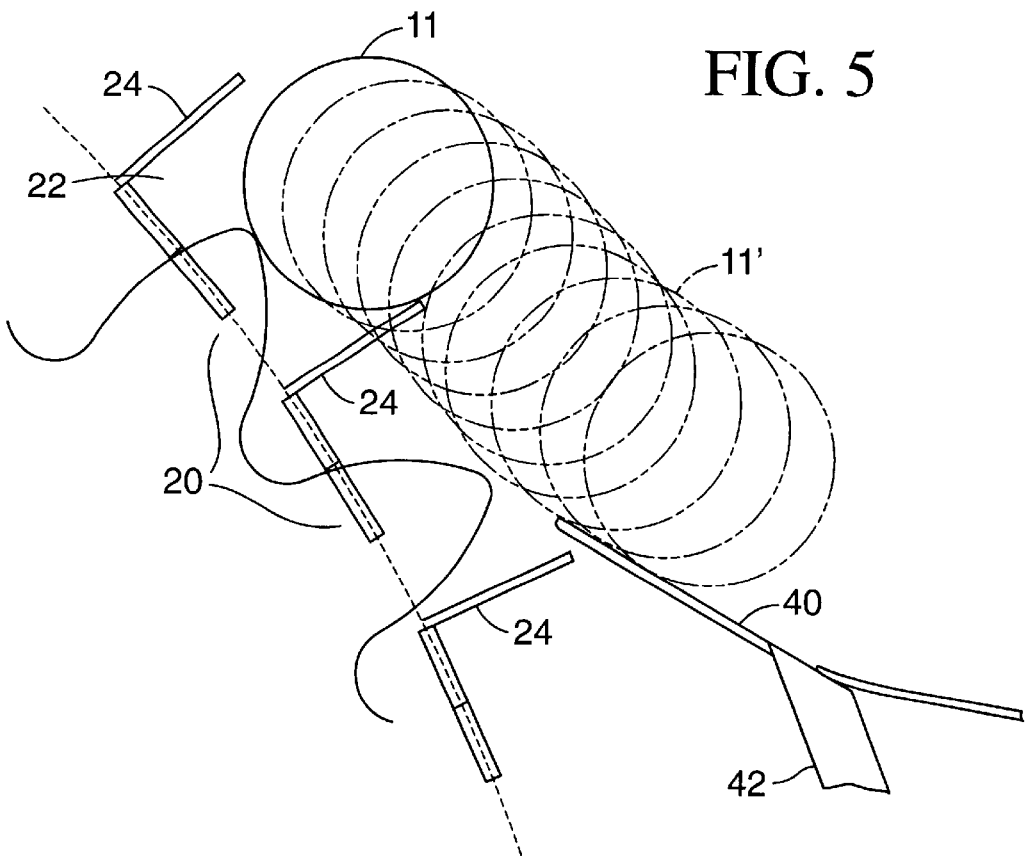
FIG. 5 is a schematic side view showing the ejector star wheel properly discharging a can.

FIG. 5 shows the forward progression of discharge of a normal, undamaged can 11. Within pocket 22, can 11 engages a lobe 20 of the star wheel ejector and is pushed outwardly of the pocket. When the can is in the position indicated by reference numeral 11', the lobe 20 has lifted the can sufficiently to cause the can to fall onto slider plate 40. Can 11' falls onto slider plate in a manner that does not cause the slider plate to move rearwardly against its spring bias. Once onto slider plate 40, can 11' rolls further along the discharge chute toward a downstream processing station.

Figure 6:
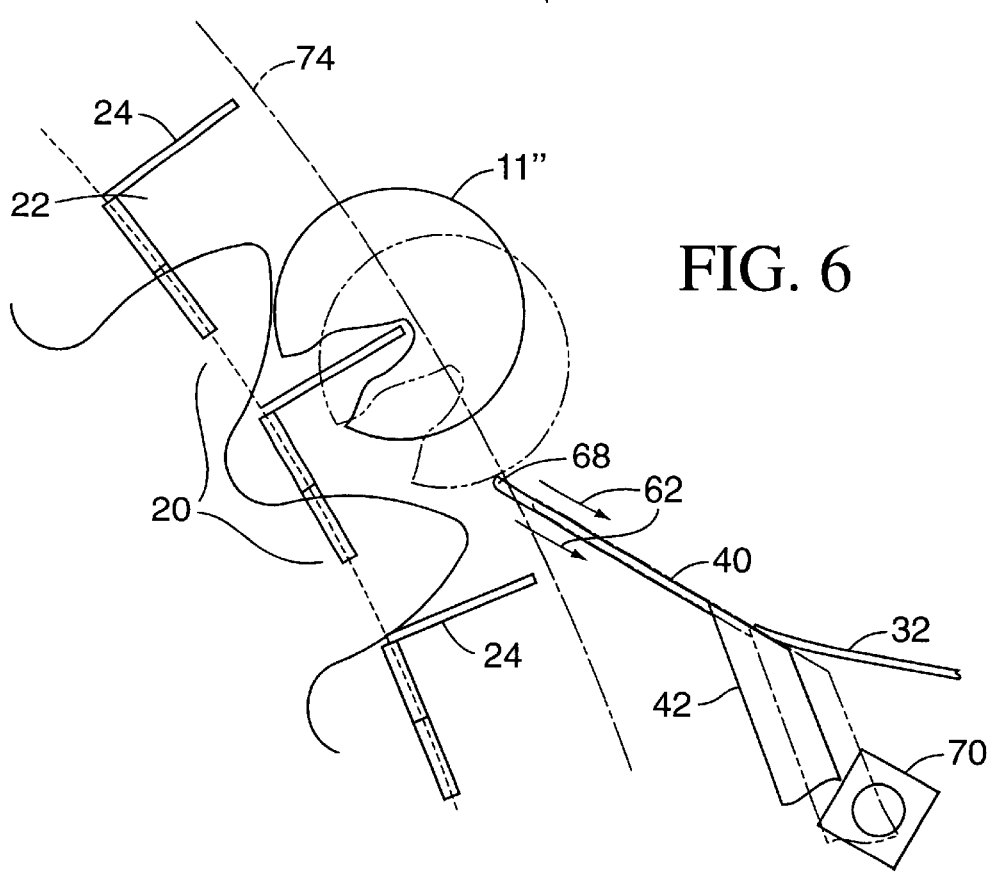
FIG. 6 is a schematic side view like FIG. 5 showing a can improperly discharging and the displacement of the discharge chute extension to signal a stuck can.

Referring to FIG. 6, shown is a damaged can 11" that has gotten wrapped around an angle iron 24. This is not an ordinary occurrence, but it does sometimes happen. In this position, can 11" misses the lobes 20 of the star wheel ejector and remains on angle iron 24, moving around the revolving path 74 that the cans make, as seen from an end of the sterilizer.

Because the leading edge 68 of slider plate 40 is positioned within the revolving path of the cans, damaged can 11" engages leading edge 68 and causes slider plate 40 to move rearwardly a short distance. Movement of slider plate 40 causes movement of frame assembly 42, which triggers sensors 70, 72 and in turn signals the control system to shut down the sterilizer. With the sterilizer shut down, an operations worker can manually retrieve the damaged can from the sterilizer by reaching his or her hand through the discharge opening.

While the spring loaded discharge chute safety mechanism is a separate mounted assembly aligned with the chute, the slider plate of the mechanism forms part of the discharge chute.

Another somewhat common misaligned can is one that gets longitudinally displaced and wrapped around the spiral rail within the sterilizer. For cans misaligned in this manner, the lobes of the star wheel ejector miss the chimes of the cans and accordingly fail to eject the cans.

Additional discharge safety mechanisms can include sensors positioned in the shell of the sterilizer at a point beyond the discharge point of the cans. The discharge point of the cans is shown by can 11' in FIG. 5. Such sensors could include a proximity sensor or any of a variety of other commonly used sensors for determining the presence nearby objects. A mechanical sensor of the type illustrated was chosen because it reliably performs in the heated environment of a sterilizer and because it also is not uncommon that there are missing cans in the line of cans, which creates gaps that a proximity sensor would read as a misaligned can, triggering a shut-down situation when none is required. However, for coolers and other types of rotary devices where sensors can withstand the environment of the device, other types of sensors may be used within the scope of the present invention. What is required is that the sensor detect the presence of a misaligned can at a point beyond the discharge point of the can.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto when read and interpreted according to accepted legal principles such as the doctrine of equivalents and reversal of parts.

What is claimed is:

1. An apparatus for monitoring proper discharge of cans from a rotary sterilizer having a rotary reel, a plurality of reel angles at the periphery of the rotary reel for moving the cans around a revolving path within the sterilizer, a spiral rail for guiding the cans from one end of the sterilizer to the other end along a spiral path, a discharge chute for receiving discharged cans from the sterilizer, and an ejector for discharging the cans onto the discharge chute, the apparatus comprising:

a sensor for detecting the presence of a can not properly discharged from the sterilizer, the sensor detecting the can at a point within the sterilizer and beyond the discharge point of the can.

2. An apparatus for monitoring proper discharge of cans from a rotary sterilizer having a rotary reel, a discharge chute for receiving discharged cans from the reel, and an ejector for discharging the cans onto the discharge chute, the apparatus comprising:

a discharge chute extension extending into a revolving path of the cans and movable in reaction to engagement with a can that is not discharged by the ejector; and a sensor detecting movement of the discharge chute extension when a can is not properly discharged from the sterilizer and engages and moves the discharge chute extension.

3. The apparatus of claim 2 wherein, the sensor provides a signal stopping operation of the sterilizer in order to retrieve the can.

4. The apparatus of claim 2 wherein, the discharge chute extension is movable at least partially in the direction of movement of the revolving path of cans.

5. The apparatus of claim 2 wherein, the discharge chute extension forms part of the discharge chute.

6. The apparatus of claim 2 wherein, the discharge cute extension includes a spring bias against which a non-discharged can must work to move the extension.

7. The apparatus of claim 5 wherein, the discharge chute extension is movable out of the revolving path of the cans upon engagement with a can not properly discharged.

8. The apparatus of claim 7 wherein, the discharge chute extension is movable along a linear path.

9. The apparatus of claim 8 wherein, the discharge chute extension includes a guide mechanism for limiting movement of the discharge chute extension along the linear path.

10. The apparatus of claim 4 wherein, the discharge chute extension includes a limit device for limiting the length of movement of the discharge chute extension.

11. The apparatus of claim 6 wherein, the spring bias is adjustable.

12. A rotary sterilizer for processing cans, comprising,
a rotary reel,
a plurality of reel angles at the periphery of the rotary reel for moving the cans around a revolving path within the sterilizer,
a spiral rail for guiding the cans from one end of the sterilizer to the other end along a spiral path,
a discharge chute for receiving discharged cans from the sterilizer,
an ejector for discharging the cans onto the discharge chute, and
a discharge chute extension apparatus for monitoring proper discharge of cans from the sterilizer, the discharge chute extension projecting into the revolving path of the cans and being movable in reaction to engagement with a can that is not discharged by the ejector.

13. The sterilizer of claim 12 wherein, the discharge chute extension is positioned in the revolving path of the cans at a point for engagement with cans not properly discharged onto the discharge chute.

14. The sterilizer of claim 13 wherein, the discharge chute extension is movable at least partially in the direction of movement of a revolving can.

15. The sterilizer of claim 13 wherein, the discharge chute extension forms part of the discharge chute.

16. The sterilizer of claim 15 wherein, the discharge chute extension is movable out of the revolving path of the cans upon engagement with a can not properly discharged.

17. The sterilizer of claim 16 wherein,
the discharge chute extension is movable along a linear path.

18. The sterilizer of claim 17 wherein,
the discharge chute extension includes a guide mechanism for limiting movement of the discharge chute extension along the linear path.

19. The sterilizer of claim 17 wherein,
the discharge chute extension includes a limit device for limiting the length of movement of the discharge chute extension.

20. The sterilizer of claim 12 and further comprising a sensor for detecting movement of the discharge chute extension.

21. The sterilizer of claim 12 wherein,
the discharge chute extension includes a spring bias against which a non-discharged can must work to move the extension.

22. The sterilizer of claim 21 wherein,
the spring bias is adjustable.

* * * * *

UNITED STATES PATENT AND TRADEMARK OFFICE
CERTIFICATE OF CORRECTION

PATENT NO.    : 6,372,189 B1                                        Page 1 of 1
DATED         : April 16, 2002
INVENTOR(S)   : Stavig et al.

It is certified that error appears in the above-identified patent and that said Letters Patent is hereby corrected as shown below:

<u>Title page,</u>
Item [73], Assignee, delete "EMC" and insert therefor -- FMC --.

Signed and Sealed this

Eighth Day of October, 2002

*Attest:*

*Attesting Officer*

JAMES E. ROGAN
*Director of the United States Patent and Trademark Office*